United States Patent
Kaiser

(10) Patent No.: US 7,842,660 B2
(45) Date of Patent: Nov. 30, 2010

(54) 4-HEPTEN-2-YL SALICYLATE AND ITS USE AS FRAGRANCE INGREDIENT

(75) Inventor: Roman Kaiser, Uster (CH)

(73) Assignee: Givaudan SA, Vernier, CH (CH)

( * ) Notice: Subject to any disclaimer, the term of this patent is extended or adjusted under 35 U.S.C. 154(b) by 33 days.

(21) Appl. No.: 11/572,218

(22) PCT Filed: Jul. 22, 2005

(86) PCT No.: PCT/CH2005/000435

§ 371 (c)(1),
(2), (4) Date: May 30, 2008

(87) PCT Pub. No.: WO2006/007755

PCT Pub. Date: Jan. 26, 2006

(65) Prior Publication Data

US 2008/0261859 A1    Oct. 23, 2008

(30) Foreign Application Priority Data

Jul. 23, 2004    (GB) ................. 0416428.1

(51) Int. Cl.
- *A61Q 13/00* (2006.01)
- *A61K 8/18* (2006.01)
- *C07C 69/76* (2006.01)
- *C07C 69/74* (2006.01)
- *C11D 3/50* (2006.01)
- *C11D 9/44* (2006.01)
- *A61K 8/00* (2006.01)

(52) U.S. Cl. ............... 512/26; 512/1; 512/20; 510/101; 424/65; 560/1; 560/8; 560/103; 560/106

(58) Field of Classification Search ........ 512/1, 512/20, 26; 510/101; 424/65; 568/300; 560/1, 8, 103, 106
See application file for complete search history.

(56) References Cited

U.S. PATENT DOCUMENTS 4,387,047 A    6/1983    Sundt et al.
5,554,588 A *  9/1996    Behan et al. .............. 512/1

FOREIGN PATENT DOCUMENTS

| EP | 1063229 A1 | 12/2000 |
|---|---|---|
| EP | 1188433 A2 | 3/2002 |
| JP | 61043106 | 3/1986 |

OTHER PUBLICATIONS

Hexyl Salicylate The Good Scents Company {http://www.thegoodscentscompany.com/data/rw1002751.html}.*
Amyl Salicylate The Good Scents Company {http://www.thegoodscentscompany.com/data/rw1012551.html}.*
cis hexen-3-yl Hexyl Salicylate The Good Scents Company {http://www.thegoodscentscompany.com/data/rw1010651.html}.*
Butyl Salicylate The Good Scents Company {http://www.thegoodscentscompany.com/data/rw1013801.html}.*
Benzyl Salicylate The Good Scents Company {http://www.thegoodscentscompany.com/data/rw1001791.html}.*
J. Flahaut et al., Helvetica Chimica Acta 61, 2275 (1978).
Russian Journal of Organic Chemistry, 1992, 28, 220-225.
Search Report from The Patent Office in Great Britain dated Nov. 4, 2004 for application GB0416428.1
International Search Report dated Sep. 28, 2005 for application PCT/CH2005/000435.
Written Opinion of the International Searching Authority for application PCT/CH2005/000435.
Steffen Arctander: "Perfume and Flavor Chemicals (Aroma Chemicals) I" 1969, S. Arctander, Montclair, N.J. (USA), XP002346575; Entry 1628: cis-3-Hexenyl Salicylate.

* cited by examiner

*Primary Examiner*—Milton I Cano
*Assistant Examiner*—Aaron Greso
(74) *Attorney, Agent, or Firm*—Norris McLaughlin & Marcus, PA

(57) ABSTRACT

The present invention is related to 4-hepten-2-yl salicylate and its use as fragrance ingredient.

5 Claims, No Drawings

4-HEPTEN-2-YL SALICYLATE AND ITS USE AS FRAGRANCE INGREDIENT

This Application is National Stage of International Application PCT/CH2005/000435 filed Jul. 22, 2005 which in turn claims priority to Application GB 0416428.1 filed Jul. 23, 2004.

The present invention refers to 4-hepten-2-yl salicylate, a method of its production and fragrance composition comprising it.

A multiplicity of salicylate esters is known from literature, some of which are used in the fragrance industry. Nevertheless, there is a constant demand in the fragrance industry for new compounds that enhance or improve on odor notes, or impart new odor notes. In particular there is an ongoing demand for long-lasting, powerful floral notes.

A widely-used salicylate ester is, for example, cis-3-hexenyl salicylate ((Z)-3-hexen-1-yl salicylate). It has been identified in carnation flower absolute and is described as possessing a sweet, green balsamic odor note.

Surprisingly, we found that the substitution of cis-3-hexenyl salicylate with a methyl group in the alpha-position to the ester group, giving 4-hepten-2-yl salicylate, has only a slight influence on the odor threshold value, whereas there is a tremendous impairment of the odor threshold value if cis-3-hexenyl salicylate is substituted by a the methyl group in beta-position to the ester, thus making 4-hepten-2-yl salicylate very useful as an substitute for the non-substituted compound. The new molecule as herein described is very valuable for the fragrance industry because of its olfactory characteristics, ist very low odor threshold value and also because of its ability to disperse very quickly throughout a room combined with a lingering effect.

As used herein "odor threshold value" means the lowest concentration of a vapor in the air which can be detected by smell. Generally speaking, it can be said that a compound with a low odor threshold value is more powerful than a compound with a high odor threshold value and thus allows the use of a very low concentration in a fragrance composition to achieve an olfactory effect.

Accordingly the present invention refers in one aspect to the use of 4-hepten-2-yl salicylate, both (Z)-4-hepten-2-yl salicylate and (E)-4-hepten-2-yl salicylate, as a fragrance ingredient.

4-Hepten-2-yl salicylate comprises one chiral centre and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC or by stereoselective synthesis.

The most desirable isomer is the (Z)-4-hepten-2-yl salicylate, which is characterized by a very crisp floral and green note reminiscent of aspects of certain lily species and frangipani. Both enantiomers have similar odor qualities, whereas the odor threshold of the (Z)-isomer is about 10 times lower than the one of the (E)-isomer, and is thus preferred.

Based on the olfactory properties of the (Z)-4-hepten-2-yl salicylate, as single isomer or in combination with the (E)-isomer, it can be used for the creation of a very broad spectrum of fragrances in combination with the broad spectrum of known fragrance ingredients, which may be selected from the extensive range of natural products and synthetic molecules currently available, such as essential oils, alcohols, aldehydes and ketones, ethers and acetals, esters and lactones, macrocycles and heterocycles. Thus, in fragrance compositions with so-called white-floral notes, it contributes or supports, respectively, aspects characteristic for lily and frangipani species and makes the composition fresher and more sparkling; in aromatic spicy-floral fragrances it may impart a desirable note of wild carnations and contribute again a sparkling freshness; added to an ionone-rich fragrance of the violet and freesia type, it makes the entire composition again very sparkling and refreshing and supports an unique floral green note. Quite generally it can be said that (Z)-4-hepten-2-yl salicylate is a powerful odorant with a remarkably low threshold value and, therefore, effects may already be obtained at dosages of 0.05 weight % based on the fragrance composition. On the other hand, this odorant is characterized by a very high integration capability and can be used at concentrations over 50 weight %.

The compound of the present invention may be employed into fragrance applications, such as perfumes, household products, laundry products, body care products and cosmetics, simply by directly mixing a fragrance composition comprising the compound with the fragrance application, or the compound may, in an earlier step be entrapped with an entrapment material such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation therein of 4-hepten-2-yl salicylate as a fragrance ingredient, either by directly admixing the compound to the application or by admixing a fragrance composition comprising the compound, which may then be mixed to a fragrance application, using conventional techniques and methods. By the addition of an olfactory effective amount of a compound of the present invention, the odor notes of a fragrance application will be improved, enhanced or modified.

Thus, the invention furthermore provides a method for improving, enhancing or modifying a fragrance application by the addition thereto of an olfactory effective amount of 4-hepten-2-yl salicylate, preferably (Z)-4-hepten-2-yl salicylate.

As used herein, "fragrance application" means any products, such as fine fragrances, e.g. eaux de perfume and eaux de toilette; household products, e.g. detergents for dishwasher, surface cleaner; laundry products, e.g. softener, bleach, detergent; body care products, e.g. shampoo, shower gel; and cosmetics, e.g. deodorants, vanishing cremes, comprising an odorant. This list of products is given by way of illustration and is not to be regarded as being in any way limiting.

The following list comprises examples of known odourant molecules and odourant natural extracts, which may be combined with 4-hepten-2-yl salicylate:

essential oils and extracts, e.g. lavender oil, juniper oil, oak moss absolute, geranium oil, jasmine absolute, patchouli oil, rose oil, sandalwood oil, lemon oil or ylang-ylang oil.

alkohols, e.g. citronellol, Ebanol®, eugenol, geraniol, Super Muguet, linalool, phenylethyl alcohol, nerolidol, 3-hexenol, Sandalore®, terpineol or Timberol®.

aldehydes and ketones, e.g. Azurone™, α-amylcinnamaldehyde, Georgywood, hydroxycitronellal, Iso E Super, Isoraldeine, Hedione®, maltol, methyl cedryl ketone, methylionone, beta-ionone, dihydrofarnesal or vanillin.

ethers and acetals, e.g. Ambrox®, geranyl methyl ether, rose oxide or Spirambrene®.

esters and lactones, e.g. benzyl acetate, cedryl acetate, γ-decalactone, Helvetolide®, γ-undecalactone or vetivenyl acetate.

macrocycles, e.g. ambrettolide, ethylene brassylate, Exaltolide® or Cosmone™.

heterocycles, e.g. isobutylchinoline.

The compound of the present invention may be prepared by transesterification of 4-heptyn-2-ol with methyl salicylate to 4-heptyn-2-yl salicylate. Selective hydrogenation of 4-heptyn-2-yl salicylate results in (Z)-4-hepten-2-yl salicylate. The (E)-isomer is available in higher yields by hydrogenation of 4-heptyn-2-ol with lithium aluminium hydride in diethylenglycol dimethyl ether to the (E)-4-hepten-2-ol and subsequent transesterification with methyl salicylate. The starting compound 4-heptyn-2-ol may be prepared according to the procedure described by J. Flahaut et al., *Helvetica Chimica Acta* 61, 2275 (1978).

The invention is now further described with reference to the following non-limiting examples.

EXAMPLE 1

4-Hepten-2-yl salicylate a) 4-Heptyn-2-yl salicylate

4-Heptyn-2-ol (22 g; 0.2 mol) and methyl salicylate (30 g; 0.2 mol) are heated under stirring and nitrogen to 120° C. Titanium(IV)isopropoxide (0.5 g ;0.02 mol) is added via syringe in one portion and the reaction is heated under reduced vacuum (600 mbar) to 150° C. meanwhile methanol is distilled off. After 24 h (75% conversion) the content of the flask is cooled to 25° C. High vacuum (0.1 Torr=0.133 mbar) is applied and the reaction mass short-path distilled, giving first 5 g of 4-heptyn-2-ol (23%) then at 118° C./0.1 Torr (0.133 mbar) 35 g of 4-heptyn-2-yl salicylate (75%).

$^1$H-NMR (400 MHz, CDCl$_3$): δ 1.10 (t, J=7.5 Hz, 3H), 1.46 (d, J=6.3 Hz, 3H), 2.14 (qt, J=7.5, 2.5 Hz, 2H), 2.52 (ddt, J=16.4, 6.8, 2.5 Hz, 1H), 2.59 (ddt, J=16.4, 5.3, 2.5 Hz, 1H), 5.24 (dqd, J=6.8, 6.3, 5.3 Hz, 1H), 6.88 (ddd, J=8.2, 7.1, 1.0 Hz, 1H), 6.97 (dd, J=8.3, 1.0 Hz, 1H), 7.45 (ddd, J=8.3, 7.1, 1.8 Hz, 1H), 7.86 (dd, J=8.2, 1.8 Hz, 1H), 10.79 (s, 1H) ppm.

IR: 1671, 1613, 1585, 1485, 1366, 1299, 1250, 1212, 1158, 1138, 1088, 1050, 1033, 756, 700.

MS: 232(M$^+$,9), 138(13), 121(100), 120(36), 94(23), 93(22), 79(37), 67(33), 65(28), 55(19), 39(21).

Odor description: white-floral scent reminiscent of certain lily species b) (Z)-4-Hepten-2-yl salicylate 4-Heptyn-2-yl salicylate (24.6 g; 0.1 mol) dissolved in 30 ml abs. ethanol are stirred over palladium on bariumsulfate (0.4 g; 0.02 mol) and under hydrogen for 3 hours. Filtration over Celite and evaporation of the ethanol under reduced pressure gives 26.2 g crude product which is distilled over a Vigreux column giving 23.5 g (96%) of a slightly yellowish oil at 98° C./0.1 Torr (0.133 mbar). Redistillation under the same conditions gives 21.6 g (88%) of colorless (Z)-4-hepten-2-yl salicylate.

$^1$H-NMR (400 MHz, CDCl$_3$): δ0.97 (t, J=7.5 Hz, 3H), 1.37 (d, J=6.3 Hz, 3H), 2.08 (qnd, J=7.5, 1.3 Hz, 2H), 2.40 (m, 1H), 2.51 (m, 1H), 5.20 (sx, J=6.3 Hz, 1H), 5.37 (dtt, J=10.9, 7.3, 1.5 Hz, 1H), 5.53 (dtt, J=10.9, 7.3, 1.5 Hz, 1H), 6.87 (ddd, J=8.1, 7.3, 1.3 Hz, 1H), 6.97 (dd, J=8.3, 1.3 Hz, 1H), 7.44 (ddd, J=8.3, 7.3, 1.8 Hz, 1H), 7.83 (dd, J=8.1, 1.8 Hz, 1H), 10.9 (s, 1H) ppm.

IR: 1669, 1613, 1586, 1485, 1366, 1299, 1249, 1212, 1157, 1089, 1047, 755, 700 cm$^{-1}$.

MS: 234(M$^+$,3), 138(17), 121(52), 120(28), 97(22), 96(44), 81(39), 65(23), 55(100), 41(22).

Odor description: crisp floral and green note reminiscent of aspects of certain lily species and frangipani.

EXAMPLE 2

(Z)-2-Methyl-3-hexen-1-yl salicylate (Z)-2-Methyl-3-hexen-1-yl salicylate was prepared from (Z)-2-methyl-3-hexen-1-ol, the synthesis of which has been described elsewhere (Russian Journal of Organic Chemistry, 1992, 28, 220-225) and methyl salicylate as described in Example 1a) above. From (Z)-2-methyl-3-hexen-1-ol (5.9 g, 0.05 mol) and methyl salicylate (7.6 g, 0.05 mol) were thus obtained after distillation at 108-112° C./0.3 mbar 7.5 g (Z)-2-methyl-3-hexen-1-yl salicylate (64%).

$^1$H-NMR (400 MHz, CDCl$_3$) :δ0.97 (t, J=7.6 Hz, 3H), 1.08 (d, J=6.8 Hz, 3H), 2.07-2.12 (m, 2H), 2.99 (qtd, J=6.8, 6.8, 0.8 Hz, 1H), 4.11-4.21 (m, 2H), 5.18 (dd, J=10.8, 1.2 Hz, 1H), 5.47 (dd, J=10.8, 0.8 Hz, 1H), 6.86 (ddd, J=8.0, 7.2, 1.2 Hz, 1H), 6.97 (dd, J=8.8, 1.2 Hz, 1H), 7.44 (ddd, J=8.8, 7.2, 2.0 Hz, 1H), 7.83 (dd, J=8.0, 2.0 Hz, 1H), 10.78 (s, 1H) ppm.

IR: 2964, 1671, 1614, 1485, 1465, 1298, 1258, 1210, 1156, 1087, 963, 754, 699 cm$^{-1}$.

MS: 234(M$^+$,2), 138(16), 121(52), 9(37), 81(31), 65(21), 55(100), 39(16).

Odor description: floral, green, watery

EXAMPLE 3

(Z)-3-Hexen-1-yl 2-hydroxy-3-methylbenzoate (Z)-3-Hexen-1-yl 2-hydroxy-3-methylbenzoate was prepared from commercially available (Z)-hex-3-en-1-ol and methyl o-cresotinate as described in Example 1a) above. From (Z)-hex-3-en-1-ol (20.0 g, 0.2 mol) and methyl o-cresotinate (33.2 g, 0.2 mol) were thus obtained after distillation at 118° C./0.2 mbar 37.2 g (Z)-3-hexen-1-yl 2-hydroxy-3-methylbenzoate (79%).

$^1$H-NMR (400 MHz, CDCl$_3$): δ0.98 (t, J=7.2 Hz, 3H), 2.09 (qi, J=7.2 Hz, 2H), 2.26 (s, 3H), 2.52 (q, J=6.8 Hz, 2H), 4.32 (t, J=6.8, 2H), 5.36-5.39 (m, 1H), 5.52-5.60 (m, 1H), 6.76 (t, J=7.6 Hz, 1H), 7.29 (d, J=7.6 Hz, 1H), 7.68 (d, J=7.6 Hz, 1H), 11.04 (s, 1H) ppm.

IR: 2963, 1667, 1614, 1390, 1327, 1288, 1246, 1170, 1150, 1083, 1010, 753, 728 cm$^{-1}$.

MS: 234(M$^+$, 9), 216(1), 152(38), 134(100), 106(31), 82(20), 77(27), 67(21), 55(59), 41(28).

Odor description: floral, balsamic, slightly green and watery

EXAMPLE 4

Determination of the GC-odor Threshold Values

According to standard procedures known to the person skilled in the art, threshold values for volatile perfumery compounds are determined on a gas chromatograph equipped with a sniff port by a panel of trained evaluators. The lowest concentration smelled by each panelist is recorded as the individual threshold value expressed in ng (absolute amount of compound delivered at the sniff port).

By way of comparison, there were also tested (Z)-2-methyl-3-hexen-1-yl salicylate and (Z)-3-hexen-1-yl 2-hydroxy-3-methylbenzoate. The objective was to show the considerable effect exerted by the position of a substituent. Under identical conditions the odor threshold value for the individual compounds was measured. The results are given below.

| Compound | odor threshold value [ng] geometric mean |
|---|---|
| (Z)-4-Hepten-2-yl salicylate | 0.77 |
| (Z)-3-Hexen-1-yl salicylate (comparative ex.) | 0.92 |
| (Z)-2-Methyl-3-hexen-1-yl salicylate (comparative ex.) | 10 |
| (Z)-3-Hexen-1-yl 2-hydroxy-3-methylbenzoate (comparative ex.) | 201 |

As can bee seen from the results above although the compounds are structurally closely related to each other, the odor threshold values are quite different. Accordingly, it was not predictable that the compound of the present invention be similar to (Z)-3-hexen-1-yl salicylate.

EXAMPLE 5

Fragrance Composition of Refreshing White-floral Character

| | Parts by weight 1/1000 |
|---|---|
| Ocimene (3,7-Dimethyl-1,2,6-octatriene) | 4 |
| Lemon oil Italy | 8 |
| cis-3-Hexenyl acetate 10% DPG | 5 |
| cis-3-Hexenol 10% DPG | 5 |
| cis-3-Hexenyl butyrate 10% DPG | 4 |
| Linalol synt. (3,7-Dimethyl-1,6-octadien-3-ol) | 100 |
| Farnesene (3,7,11-Trimethyl-1,3,6,10-dodecatetraene) | 15 |
| Methyl salicylate | 3 |
| Benzyl alcohol | 30 |
| Jasmone (3-Methyl-2-(2-pentenyl)-2-cyclopenten-1-one) | 3 |
| beta-Ionone | 5 |
| Phenylethyl 2-methylbutyrate | 5 |
| Dihydrofarnesal | 20 |
| Nerolidol (3,7,11-Trimethyl-1,6,10-dodecatrienol-3) | 35 |
| Farnesol | 40 |
| cis-3-Hexenyl benzoate | 40 |
| Indole | 7 |
| Benzyl benzoate | 150 |
| Benzyl salicylate | 300 |
| Methyl anthranilate | 1 |
| cis-3-Hexenyl cis-3-hexenoate 10% DPG | 10 |
| Gardenol | 8 |
| Dihydro-beta-ionone | 1 |
| Hedione (Methyl dihydrojasmonate) | 30 |
| Anapear (Methyl (E)-4,7-octadienoate) 10% DPG | 5 |
| Damascenone 1% DPG | 1 |
| Myraldyl acetate | 50 |
| Dipropylene glycol (DPG) | 115 |
| Total | 1000 |

Addition of 100 parts of (Z)-4-hepten-2-yl salicylate makes the above composition much more sparkling and lush and a desired note of frangipani and lily species becomes much more developed.

EXAMPLE 6

Fragrance Composition of Spicy White-floral Character

| | Parts per weight 1/1000 |
|---|---|
| cis-3-Hexenyl acetate | 1 |
| cis-3-Hexenol | 1 |
| Decanal | 1 |
| Linalyl acetate synt. | 5 |
| Bornyl acetate laevo | 5 |
| Methyl salicylate | 2 |
| Rhodinol pur | 5 |
| Benzyl alcohol | 20 |
| Phenylethyl alcohol | 70 |
| Sandalore (5-(2,2,3-Trimethyl-3-cyclopentenyl)-3-methylpentan-2-ol) | 5 |
| Dihydrofarnesal | 40 |
| Nerolidol (3,7,11-Trimethyl-1,6,10-dodecatrien-3-ol) | 30 |
| Vetynal | 5 |
| Amyl salicylate | 10 |
| Cinnamic alcohol | 35 |
| Isoeugenol | 30 |
| cis-3-Hexenyl benzoate | 5 |
| Indole | 5 |
| Vanilline | 5 |
| Benzyl benzoate | 100 |
| Phenylethyl benzoate | 80 |
| Benzyl salicylate | 200 |
| cis-3-Hexenyl cis-3-hexenoate 10% DPG | 3 |
| Linalol | 80 |
| Ocimene | 3 |
| Methyl benzoate | 3 |
| cis-3-Hexenyl benzoate | 35 |
| Dipropylene glycol (DPG) | 216 |
| Total | 1000 |

Addition of 100 parts of (Z)-4-hepten-2-yl salicylate makes above composition much more sparkling, lighter and fresher. Furthermore, it helps to develop a very attractive note of wild carnation and supports in general very much the desired spicy white-floral note.

EXAMPLE 7

Fragrance Composition with Violet and Freesia Character

| | Parts by weight 1/1000 |
|---|---|
| Dihydro-beta-ionone | 65 |
| alpha-Ionone | 10 |
| beta-Ionone | 200 |
| Myraldyl acetate | 150 |
| Rhodinol pur | 30 |
| Citral | 3 |
| trans-2-Dodecenal 10% DPG | 3 |
| cis-3-Hexenyl acetate 10% DPG | 4 |
| Dodecanal 10% DPG | 3 |
| Dihydrofarnesal | 60 |
| alpha-Terpineol | 60 |

-continued

|  | Parts by weight 1/1000 |
| --- | --- |
| Linalol synt. | 100 |
| Farnesol | 45 |
| Hydroxycitronellal | 70 |
| Dipropylene glycol (DPG) | 197 |
| Total | 1000 |

Addition of 60 parts of (Z)-4-hepten-2-yl salicylate to the above fragrance accord makes the composition lush, sparkling and refreshing floral with a delicate green-fruity shade.

The invention claimed is:

1. (Z)-4-hepten-2-yl salicylate.

2. A fragrance composition comprising (Z)-4-hepten-2-yl salicylate.

3. A method of manufacturing a fragrance application comprising the step of incorporating an effective amount of (Z)-4-hepten-2-yl salicylate into the fragrance application.

4. (Z)-4-hepten-2-yl salicylate according to claim 1, wherein the (Z)-4-hepten-2-yl salicylate has an odor threshold value expressed in ng of about 0.77.

5. (Z)-4-hepten-2-yl salicylate according to claim 1, wherein the (Z)-4-hepten-2-yl salicylate has a floral odor note.

* * * * *